US005780435A

United States Patent [19]
Garnick et al.

[11] Patent Number: 5,780,435
[45] Date of Patent: Jul. 14, 1998

[54] METHODS FOR TREATING PROSTATE CANCER WITH LHRH-R ANTAGONISTS

[75] Inventors: Marc B. Garnick; Christopher J. Molineaux, both of Brookline; Malcolm L. Gefter, Lincoln, all of Mass.

[73] Assignee: Praecis Pharmaceuticals Incorporated, Cambridge, Mass.

[21] Appl. No.: 573,109

[22] Filed: Dec. 15, 1995

[51] Int. Cl.$^6$ ............................................. A61K 38/09

[52] U.S. Cl. ...................... 514/15; 514/16; 514/425; 514/522; 514/629; 514/800; 530/328

[58] Field of Search ........................ 514/16, 15, 800, 514/425, 522, 629; 530/328

[56] References Cited

U.S. PATENT DOCUMENTS

| | | | |
|---|---|---|---|
| 4,659,695 | 4/1987 | Labrie | 514/15 |
| 4,666,885 | 5/1987 | Labrie | 514/15 |
| 4,760,053 | 7/1988 | Labrie | 514/15 |
| 4,775,660 | 10/1988 | Labrie et al. | 514/15 |
| 4,775,661 | 10/1988 | Labrie | 514/15 |
| 5,023,234 | 6/1991 | Labrie | 514/15 |
| 5,064,813 | 11/1991 | Labrie | 514/15 |
| 5,116,615 | 5/1992 | Gokcen et al. | 424/94.2 |
| 5,130,137 | 7/1992 | Crowley, Jr. | 424/422 |
| 5,180,711 | 1/1993 | Hodgen | 514/15 |
| 5,372,996 | 12/1994 | Labrie | 514/15 |

FOREIGN PATENT DOCUMENTS

| | | |
|---|---|---|
| 0 413 209 A1 | 2/1991 | European Pat. Off. . |
| 0 678 577 A2 | 10/1995 | European Pat. Off. . |
| WO 91/00731 | 1/1991 | WIPO . |

OTHER PUBLICATIONS

Emons, G. et al. "The Use of Luteinizing Hormone Releasing Hormone Agonists and Antagonists in Gynaecological Cancers", Human Reproduction Update., vol. 9, No. 7, pp. 1364–1379, 1994.

Pinski, J. et al. "Inhibitory Effects of Analogs of Luteinizing Hormone–Releasing Hormone On The Growth of The Androgen–Indepedent Dunning R–3327–AT–1 Rat Prostate Cancer", Int. J. Cancer: 59, 51–55 (1994).

Andros, E. et al., "Neoadjuvant Hormonal Therapy in Stage C Adenocarcinoma of the Prostate," Clin. Invest. Med. vol. 16:6, 510–515 (1993).

Couzinet, B. et al., "Effects of Gonadotrophin Releasing Hormone Antagonist and Agonist on the Pulsatile Release of Gonadotrophins and X–Subunit in Postmenopausal Women," Clinical Endocrinology vol. 34, 477–483 (1991).

Illions, E. et al., "Evaluation of the Impact of Concurrent Gonadotropin–Releasing Hormone (GnRH) Antagonist Administration on GnRH Agonist–Induced Gonadotrope Desensitization," Fertility and Sterility, vol. 64:4, 848–854 (1995).

Labrie, F. et al., "Combination Therapy for Prostate Cancer," Cancer Supplement vol. 71:3, 1059–1067 (1993).

Labrie, F. et al., "Downstaging by Combination Therapy with Flutamide and an LHRH Agonist before Radical Prostatectomy," Cancer Surveys vol. 23, 149–156 (1995).

Pinski, J. et al., "Blockade of the LH Response Induced by the Agonist D–Trp–6–LHRH in Rats by a Highly Potent LH–RH Antagonist SB–75," The Prostate vol. 20, 213–224 (1992).

Sharma, O.P. et al., "The Gonadotropin–Releasing Hormone (GnRH) Agonist–Induced Initial Rise of Bioactive LH and Testosterone can be Blunted in a Dose–Dependent Manner by GnRH Antagonist in the Non–Human Primate," Urological Research vol. 20, 317–321 (1992).

Smith, P.H. et al., "Hormone Therapy: An Overview," Cancer Surveys vol. 23, 171–181 (1995).

Solomon, M.H. et al., "Hormone Ablation Therapy as Neoadjuvant Treatment to Radical Prostatectomy," Clin. Invest. Med. vol. 16:6, 532–538 (1993).

Primary Examiner—Richard L. Raymond
Attorney, Agent, or Firm—Lahive & Cockfield, LLP; Giulio A. DeConti, Jr.; Catherine J. Kara

[57] ABSTRACT

Methods for treating prostate cancer are disclosed. The methods of the invention generally feature administration to a subject of an LHRH-R antagonist, in combination with a second therapy. In one embodiment, this second therapy is performance of a procedure that removes or destroys prostatic tumor tissue, such as a radical prostatectomy, cryosurgery or X-ray therapy (external or interstitial). In another embodiment, the second therapy is treatment with an LHRH-R agonist, either simultaneous with or subsequent to LHRH-R antagonist therapy. The methods of the invention can further involve administering an antiandrogen and/or an inhibitor of sex steroid biosynthesis to the subject in combination with the LHRH-R antagonist.

22 Claims, No Drawings

METHODS FOR TREATING PROSTATE CANCER WITH LHRH-R ANTAGONISTS

BACKGROUND OF THE INVENTION

Prostate cancer is a serious condition that affects increasing numbers of men worldwide. About one-third of all men have at least some cancerous prostatic cells at age 50, with the incidence increasing to as many as 90 percent of men at age 90. In the United States alone, about 40,000 men die each year from prostate cancer.

Prostate cancer is a sex hormone dependent cancer; that is, the growth of the cancer is promoted by male hormones (e.g., androgens such as testosterone and dihydrotestosterone). Removal of the testes (castration) was for many years the standard method of preventing the secretion of male hormones by the gonads, as a means for reducing growth of the cancer. More recently, secretion of male hormones has been perturbed by chemical means by interfering with production of luteinizing hormone (LH), which regulates the synthesis of male hormones. Luteinizing hormone releasing hormone (LHRH) is a natural hormone produced by the hypothalamus that interacts with luteinizing hormone releasing hormone receptor (LHRH-R) in the pituitary to stimulate production of LH. To decrease LH production, superagonists of the luteinizing hormone releasing hormone receptor (LHRH-R), such as leuprolide and goserelin, have been used. However, such LHRH-R superagonists initially act to stimulate LH release and only after prolonged treatment act to desensitize LHRH-R such that LH is no longer produced. The initial stimulation of LH production by the superagonist leads to an initial surge in the production of male hormones such that the initial response to superagonist therapy is aggravation, rather than amelioration, of the patient's condition (e.g., tumor growth increases). This phenomenon, known as the "flare reaction", can last for two to four weeks. Additionally, each successive administration of the superagonist can cause a small LH surge (known as the "acute-on chronic" phenomenon) that again can worsen the condition. The "flare reaction" prohibits the use of LHRH-R superagonists in the treatment of late stage prostatic cancer patients where the cancer has metastasized to the spinal cord, since the initial stimulation of cancer growth would cause nerve trunk compression and damage. To ensure that a candidate patient for superagonist therapy does not have spinal cord metastasis, additional diagnostic tests must be conducted, such as magnetic resonance imaging or a spinal CAT scan, which adds to the cost of superagonist therapy.

One approach that has been taken to avoid the "flare reaction" has been to combine administration of an LHRH-R superagonist with an antiandrogen, such as flutamide, known as total androgen ablation therapy (AAT). Hormonal therapy with an LHRH-R superagonist in combination with an antiandrogen has been used as a pre-treatment prior to radical prostatectomy, known as neoadjuvant therapy. The use of antiandrogens, however, is associated with serious hepatic and gastrointestinal side effects.

Accordingly, methods for treating prostate cancer that are more effective than those utilizing LHRH-R superagonists and that both avoid the occurrence of the "flare reaction" and do not require the use of antiandrogens (thus avoiding the side-effects of using antiandrogens) are needed.

SUMMARY OF THE INVENTION

The present invention features methods of treating prostate cancer designed to reduce or eliminate the flare reaction that occurs with current prostate cancer therapies utilizing LHRH-R superagonists. Because the treatment methods of the invention avoid the flare reaction, they are applicable to a wider number of prostatic cancer patients than is LHRH-R superagonist therapy (e.g., the methods of the invention can be applied to patients with spinal cord metastasis). Moreover, certain expensive diagnostic tests that must be performed prior to initiating LHRH-R superagonist therapy may be eliminated when the methods of the invention are used (e.g., an MRI or spinal CAT scan, which must be performed to rule out spinal cord metastasis before initiating LHRH-R superagonist therapy). Still further the methods of the invention can be performed without the use of an antiandrogen (although in certain optional embodiments an antiandrogen may be used) and therefore these methods cap avoid the side-effects that occur with antiandrogen use.

The methods of the invention generally feature administration of an LHRH-R antagonist in combination with a second therapy. In one embodiment, this second therapy is a procedure to remove or destroy tumor tissue, such as a radical prostatectomy, cryosurgery or X-ray therapy (external or interstitial). Preferably, the LHRH-R antagonist is administered to the subject prior to performing the procedure that removes or destroys prostatic tumor tissue. In a particularly preferred embodiment, the LHRH-R antagonist is administered to the subject for 3 to 6 months prior to performing the procedure that removes or destroys prostatic tumor tissue. In another embodiment of the methods of the invention, the second therapy is treatment with an LHRH-R agonist (e.g., a superagonist, such as leuprolide, goserelin or decapeptyl). In this embodiment, the LHRH-R antagonist preferably is administered to the subject prior to initiating therapy with the LHRH-R agonist. Once LHRH-R agonist therapy has begun, LHRH-R antagonist therapy can be continued (i.e., the antagonist and agonist can be coadministered) or discontinued (i.e., first the LHRH-R antagonist is administered alone and then the LHRH-R agonist is administered alone). Moreover, the two-step combination methods of the invention can further be combined with additional treatments, such as administration of an antiandrogen or administration of one or more inhibitors of sex steroid biosynthesis.

DETAILED DESCRIPTION OF THE INVENTION

The present invention provides combination methods for treatment of prostate cancer in a subject in need thereof and compositions for use in such treatments.

As used herein, a "subject" is intended to include warm-blooded animals, preferably mammals, including humans.

The term "LHRH-R antagonist", as used herein, refers to a compound that inhibits the luteinizing hormone releasing hormone receptor such that release of luteinizing hormone is inhibited. LHRH-R antagonists have been described in the art; see e.g., U.S. Pat. No. 5,470,947 to Folkers et al.; Folkers et al., PCT Publication No. WO 89/01944; U.S. Pat. No. 5,413,990 to Haviv; U.S. Pat. No. 5,300,492 to Haviv; U.S. Pat. No. 5,371,070 to Koerber et al.; U.S. Pat. No. 5,296,468 to Hoeger et al.; U.S. Pat. No. 5,171,835 to Janaky et al.; U.S. Pat. No. 5,003,011 to Coy et al.; U.S. Pat. No. 4,431,635 to Coy; U.S. Pat. No. 4,992,421 to De et al.; U.S. Pat. No. 4,851,385 to Roeske; U.S. Pat. No. 4,801,577 to Nestor, Jr. et al.; and U.S. Pat. No. 4,689,396 to Roeske et al. Preferred LHRH-R antagonists are those having low histamine-releasing activity (e.g., an $ED_{50}$ for histamine release in a standard in vitro histamine release assay of at least 3 µg/ml, more preferably at least 5 µg/ml, and still more preferably at least 10 µg/ml) and that exhibit water solubility. Preferred LHRH-R antagonists with low histamine-releasing activity and water solubility include compounds disclosed in U.S. patent application Ser. No. 08/480,494, filed on Jun. 7, 1995, the entire contents of which is expressly incorporated herein by reference.

TABLE I

LHRH Antagonists

| Compound | Sequence | AO activity (AOA) | Histamine release |
|---|---|---|---|
| 3341 | Ac-D-Nal$^1$, 4-Cl-D-Phe$^2$, D-Pal$^3$, D-Gln$^6$—Lys(iPr)$^8$, D-Ala$^{10}$—LHRH.TFA | 4/10@1 µg<br>2/10@2 µg | 106 |
| 3342 | Ac-D-Nal$^1$, 4-Cl-D-Phe$^2$, D-Pal$^3$, D-Asn$^6$—Lys(iPr)$^8$, D-Ala$^{10}$—LHRH.TFA | 2/10@2 µg | 126 |
| 3343 | Ac-D-Nal$^1$, 4-Cl-D-Phe$^2$, D-Pal$^3$, D-Thr$^6$—Lys(iPr)$^8$, D-Ala$^{10}$—LHRH.TFA | 5/10@1 µg | 62 |
| 3344 | Ac-D-Nal$^1$, 4-Cl-D-Phe$^2$, D-Pal$^3$, D-Cit$^6$—Lys(iPr)$^8$, Pip$^9$-D-Ala$^{10}$—LHRH.TFA | 9/10@1 µg | 32 |
| 3361 | Ac-D-Nal$^1$, 4-Cl-D-Phe$^2$, D-Pal$^3$, D-Glu-(Taurine)$^6$—Lys(iPr)$^8$, D-Ala$^{10}$—LHRH.TFA | 1/8@5 µg | 131 |
| 3362 | Ac-D-Nal$^1$, 4-Cl-D-Phe$^2$, D-Pal$^3$, D-Cit$^6$—Lys(iPr)$^8$—LHRH.TFA | 4/8@1 µg | 22 |
| 3363 | Ac-D-Nal$^1$, 4-Cl-D-Phe$^2$, D-Pal$^3$, D-Cit$^6$—Lys(iPr)$^8$, Pip$^9$—LHRH.TFA | 6/8@1 µg | 25 |
| 3364 | Ac-D-Nal$^1$, 4-Cl-D-Phe$^2$, D-Pal$^3$, D-Phe-(4-NO$_2$)$^6$—Lys(iPr)$^8$, D-Ala$^{10}$—LHRH.TFA | 6/8@1 µg | 14 |
| 3365 | Ac-D-Nal$^1$, 4-Cl-D-Phe$^2$, D-Pal$^3$, D-Cit$^6$—Lys(iPr)$^8$, ProNHEt$^9$-des-Gly$^{10}$—LHRH.TFA | | 24 |
| 3366 | Ac-D-(or L)-9-anthryl-Ala$^1$, 4-Cl-D-Phe$^2$, D-Pal$^3$, D-Cit$^6$—Lys(iPr)$^8$, D-Ala$^{10}$—LHRH.TFA | 6/8@5 µg | |
| 3367 | Ac-L-(or D)-9-anthryl-Ala$^1$, 4-Cl-D-Phe$^2$, D-Pal$^3$, D-Cit$^6$—Lys(iPr)$^8$, D-Ala$^{10}$—LHRH.TFA | 7/8@5 µg | |
| 3368 | Ac-D-(or L)-Ada-Ala$^1$, 4-Cl-D-Phe$^2$, D-Pal$^3$, D-Cit$^6$—Lys(iPr)$^8$, D-Ala$^{10}$—LHRH.TFA | 5/8@5 µg | 34 |
| 3369 | Ac-L-(or D)-Ada-Ala$^1$, 4-Cl-D-Phe$^2$, D-Pal$^3$, D-Cit$^6$—Lys(iPr)$^8$, D-Ala$^{10}$—LHRH.TFA | 7/8@5 µg | 93 |
| 3423A | Ac-D-Nal$^1$, 4-Cl-D-Phe$^2$, D-Pal$^3$, D-Lys-(Glc)$^6$—Lys(iPr)$^8$, D-Ala$^{10}$—LHRH.TFA | 7/10@0.5 µg<br>2/10@1 µg<br>0/10@2 µg | 52 |
| 3428 | Ac-D-Nal$^1$, 4-Cl-D-Phe$^2$, D-Pal$^3$, D-Pal(1-Bu)$^6$, Lys-(iPr)$^8$, D-Ala$^{10}$—LHRH.TFA | 1/8@1 µg | |
| 3429 | Ac-D-Nal$^1$, 4-Cl-D-Phe$^2$, D-Pal$^3$, D-Pal(Bzl)$^6$, Lys-(iPr)$^8$, D-Ala$^{10}$—LHRH.TFA | 0/8@1 µg<br>4/8@0.5 µg | 6.0 |
| 3430 | Ac-D-Nal$^1$, 4-Cl-D-Phe$^2$, D-Pal$^3$, Pal$^5$, D-Pal(iPr)$^6$, Lys(iPr)$^8$, D-Ala$^{10}$—LHRH.TFA | 3/8@1 µg | 10 |
| 3431 | Ac-D-Nal$^1$, 4-Cl-D-Phe$^2$, D-Pal$^3$, Cit$^5$, D-Cit$^6$, Lys-(iPr)$^8$, D-Ala$^{10}$—LHRH.TFA | 6/8@1 µg | |
| 3432 | Ac-D-Nal$^1$, 4-Cl-D-Phe$^2$, D-Pal$^3$, Pal$^5$, D-Cit$^6$, Lys-(iPr)$^8$, D-Ala$^{10}$—LHRH.TFA | 7/8@1 µg | |
| 3433 | Ac-D-Nal$^1$, 4-Cl-D-Phe$^2$, D-Pal$^3$, Cit$^5$, D-Pal$^6$, Lys-(iPr)$^8$, D-Ala$^{10}$—LHRH.TFA | 5/8@1 µg | |
| 3434 | Ac-D-Nal$^1$, 4-Cl-D-Phe$^2$, D-Pal$^3$, Asn$^4$, Tyr$^5$, D-Cit$^6$, Lys(iPr)$^8$, D-Ala$^{10}$—LHRH.TFA | 4/8@1 µg | |
| 3435 | Ac-D-Nal$^1$, 4-Cl-D-Phe$^2$, D-Pal$^3$, Cit$^5$, D-Pal(iPr)$^6$, Lys(iPr)$^8$, D-Ala$^{10}$—LHRH.TFA | 7/8@1 µg | |
| 3436 | Ac-D-Nal$^1$, 4-Cl-D-Phe$^2$, D-Pal$^3$, D-HomoArg(NO$_2$)$^6$, Lys(iPr)$^8$, D-Ala$^{10}$—LHRH.TFA | 7/8@1 µg | |
| 3437 | Ac-D-Nal$^1$, 4-Cl-D-Phe$^2$, D-Pal$^3$, D-Lys(Glycolyl)$^6$, Lys(iPr)$^8$, D-Ala$^{10}$—LHRH.TFA | 7/8@1 µg | |
| 3438 | Ac-D-Nal$^1$, 4-Cl-D-Phe$^2$, D-Pal$^3$, D-Lys(iPrPic)$^6$, Lys(iPr)$^8$, D-Ala$^{10}$—LHRH.TFA | 2/8@1 µg | 5.6 |
| 3439 | Ac-D-Nal$^1$, 4-Cl-D-Phe$^2$, D-Pal$^3$, D-Lys(HomoPro)$^6$, Lys(iPr)$^8$, D-Ala$^{10}$—LHRH.TFA | 2/8@1 µg | |
| 2958 | Ac-D-Nal$^1$, 4-Cl-D-Phe$^2$, D-Pal$^3$, D-Pal(iPr)$^6$, Lys-(iPr)$^8$, D-Ala$^{10}$—LHRH.TFA | | |
| 3440 | Ac-D-Nal$^1$, 4-Cl-D-Phe$^2$, D-Pal$^3$, D-Lys(3-pyridine-acetic)$^6$, Lys(iPr)$^8$, D-Ala$^{10}$—LHRH.TFA | 2/8@1 µg | |
| 3441 | Ac-D-Nal$^1$, 4-Cl-D-Phe$^2$, D-Pal$^3$, D-Lys(2-ClNic)$^6$, Lys(iPr)$^8$, D-Ala$^{10}$—LHRH.TFA | 8/8@1 µg | |
| 3442 | Ac-N$^\alpha$Me-D-Nal$^1$, 4-Cl-D-Phe$^2$, D-Pal$^3$, D-Cit$^6$, Lys(iPr)$^8$, D-Ala$^{10}$—LHRH.TFA | 7/8@1 µg | |
| 3502 | Ac-D-Nal$^1$, 4-Cl-D-Phe$^2$, D-Pal$^3$, Lys(Otac)$^5$, D-Lys(Otac)$^6$, Lys(iPr)$^8$, D-Ala$^{10}$—LHRH.TFA | 6/8@1 µg | |
| 3503 | Ac-D-Nal$^1$, 4-Cl-D-Phe$^2$, D-Pal$^3$, Lys(ONic)$^5$, D-Lys(ONic)$^6$, Lys(iPr)$^8$, D-Ala$^{10}$—LHRH.TFA | 6/8@1 µg | |

TABLE I-continued

LHRH Antagonists

| Compound | Sequence | AO activity (AOA) | Histamine release |
|---|---|---|---|
| 3504 | Ac-D-Nal$^1$, 4-Cl-D-Phe$^2$, D-Pal$^3$, Lys(Pyz)$^5$, D-Lys-(Pyz)$^6$, Lys(iPr)$^8$, D-Ala$^{10}$—LHRH.TFA | 4/8@1 μg | |
| 3552 | Ac-D-Nal$^1$, 4-Cl-D-Phe$^2$, D-Pal$^3$, D-Glu$^6$, Lys(iPr)$^8$, D-Ala$^{10}$—LHRH.TFA | 8/8@1 μg | |
| 3505 | Ac-D-Nal$^1$, 4-Cl-D-Phe$^2$, D-Pal$^3$, D-Lys$^6$, Lys(iPr)$^8$, D-Ala$^{10}$—LHRH.TFA | 5/8@1 μg | |
| 3506 | Ac-D-Nal$^1$, 4-Cl-D-Phe$^2$, D-Pal$^3$, D-Lys(Gulonyl)$^6$, Lys(iPr)$^8$, D-Ala$^{10}$—LHRH.TFA | 4/8@1 μg | |
| 3553 | Ac-D-Nal$^1$, 4-Cl-D-Phe$^2$, D-Pal$^3$, D-Lys(iPrNic)$^5$, D-Lys(iPrNic)$^6$, Lys(iPr)$^8$, D-Ala$^{10}$—LHRH.TFA | 8/8@1 μg | |
| 3507 | Ac-D-Nal$^1$, 4-Cl-D-Phe$^2$, D-Pal$^3$, D-Lys(ONic)$^6$ Lys(iPr)$^8$, D-Ala$^{10}$—LHRH.TFA | 1/8@1 μg | |
| 3508 | Ac-D-Nal$^1$, 4-Cl-D-Phe$^2$, D-Pal$^3$, D-Lys(OTac)$^6$ Lys(iPr)$^8$, D-Ala$^{10}$—LHRH.TFA | 0/8@1 μg 6/8@0.5 μg | |
| 3509 | Ac-D-Nal$^1$, 4-Cl-D-Phe$^2$, D-Pal$^3$, D-Lys(Pyz)$^6$ Lys(iPr)$^8$, D-Ala$^{10}$—LHRH.TFA | | |
| 3510 | Ac-D-Nal$^1$, 4-Cl-D-Phe$^2$, D-Pal$^3$, D-Lys(nBuNic)$^6$, Lys(iPr)$^8$, D-Ala$^{10}$—LHRH.TFA | | |
| 3511 | Ac-D-Nal$^1$, 4-Cl-D-Phe$^2$, D-Pal$^3$, D-Glu(Amp)$^6$, Lys(iPr)$^8$, D-Ala$^{10}$—LHRH.TFA | 7/8@1 μg | |
| 3543 | Ac-D-Nal$^1$, 4-Cl-D-Phe$^2$, D-Pal$^3$, D-Glu(Dea)$^6$, Lys(iPr)$^8$, D-Ala$^{10}$—LHRH.TFA | 6/8@1 μg | |
| 3563 | Ac-D-Nal$^1$, 4-Cl-D-Phe$^2$, D-Pal$^3$, Lys(pGlu)$^5$, D-Lys(pGlu)$^6$, Lys(iPr)$^8$, D-Ala$^{10}$—LHRH.TFA | | |
| 3540 | Ac-D-Nal$^1$, 4-Cl-D-Phe$^2$, D-Pal$^3$, N$^\alpha$Me—Tyr$^5$, D-Pal(iPr)$^6$, Lys(iPr)$^8$, D-Ala$^{10}$—LHRH.TFA | | |
| 3541 | Ac-D-Nal$^1$, C$^\alpha$Me-4Cl-Phe$^2$, D-Pal$^3$, N$^\alpha$Me—Tyr$^5$, D-Pal(iPr)$^6$, Lys(iPr)$^8$, D-Ala$^{10}$—LHRH.TFA | 1/8@1 μg | |
| 3554 | Ac-D-Nal$^1$, 4-Cl-D-Phe$^2$, D-Pal$^3$, Lys(CNa)$^6$, Lys-(iPr)$^8$, D-Ala$^{10}$—LHRH.TFA | | |
| 3542 | Ac-D-Nal$^1$, 4-Cl-D-Phe$^2$, D-Pal$^3$, D-Glu(PEG)$^6$, Lys(iPr)$^8$, D-Ala$^{10}$—LHRH.2TFA | 7/8@2 μg | |
| 3565 | Ac-D-Nal$^1$, 4-Cl-D-Phe$^2$, D-Pal$^3$, D-Lys(Oxa)$^6$, Lys(iPr)$^8$, D-Ala$^{10}$—LHRH.2TFA | | |
| 3551 | Ac-D-Nal$^1$, 4-Cl-D-Phe$^2$, D-Pal$^3$, Lys(CNa)$^5$, D-Lys(CNa)$^6$, Lys(iPr)$^8$, D-Ala$^{10}$—LHRH.2TFA | 6/8@1 μg | |
| 3544 | Ac-D-Nal$^1$, 4-Cl-D-Phe$^2$, D-Pal$^3$, Lys(ClNic)$^5$, D-Lys(ClNic)$^6$, Lys(iPr)$^8$, D-Ala$^{10}$—LHRH.2TFA | 6/8@1 μg | |
| 3555A | Ac-D-Nal$^1$, 4-Cl-D-Phe$^2$, D-Pal$^3$, D-Lys(Ac)$^6$, Lys(iPr)$^8$, D-Ala$^{10}$—LHRH.2TFA | | |
| 3564 | Ac-D-Nal$^1$, 4-Cl-D-Phe$^2$, D-Pal$^3$, D-Glu(Tris)$^6$, Lys(iPr)$^8$, D-Ala$^{10}$—LHRH.2TFA | | |
| 3545 | Ac-D-Nal$^1$, 4-Cl-D-Phe$^2$, D-Pal$^3$, D-Gln(iPr)$^6$, Lys(iPr)$^8$, D-Ala$^{10}$—LHRH.2TFA | 7/8@1 μg | |
| 3550 | Ac-D-Nal$^1$, 4-Cl-D-Phe$^2$, D-Pal$^3$, D-Glu(CSer)$^6$, Lys(iPr)$^8$, D-Ala$^{10}$—LHRH.2TFA | 6/8@1 μg | |
| 3549 | Ac-D-Nal$^1$, 4-Cl-D-Phe$^2$, D-Pal$^3$, D-Glu(Mop)$^6$, Lys(iPr)$^8$, D-Ala$^{10}$—LHRH.2TFA | 6/8@1 μg | |
| 3548 | Ac-D-Nal$^1$, 4-Cl-D-Phe$^2$, D-Pal$^3$, Lys$^5$, D-Pal(iPr)$^6$, Lys(iPr)$^8$, D-Ala$^{10}$—LHRH.4TFA | 6/8@1 μg | |
| 3566 | Ac-D-Nal$^1$, 4-Cl-D-Phe$^2$, D-Pal$^3$, Lys(Nic)$^5$, D-Pal-(iPr)$^6$, Lys(iPr)$^8$, D-Ala$^{10}$—LHRH.3TFA | | |
| 3567 | Ac-D-Nal$^1$, 4-Cl-D-Phe$^2$, D-Pal$^3$, Lys(Ac)$^5$, D-Pal-(iPr)$^6$, Lys(iPr)$^8$, D-Ala$^{10}$—LHRH.3TFA | | |
| 3568 | Ac-D-Nal$^1$, 4-Cl-D-Phe$^2$, D-Pal$^3$, D-Glu(DEGA)$^6$, Lys(iPr)$^8$, D-Ala$^{10}$—LHRH.2TFA | | |
| 3547 | Ac-D-Nal$^1$, 4-Cl-D-Phe$^2$, D-Pal$^3$, Lys(Nic)$^5$, D-Pal-(Bzl)$^6$, Lys(iPr)$^8$, D-Ala$^{10}$—LHRH.3TFA | 6/8@1 μg | |
| 3569 | Ac-D-Nal$^1$, 4-Cl-D-Phe$^2$, D-Pal$^3$, Lys(Ac)$^5$, D-Pal-(Bzl)$^6$, Lys(iPr)$^8$, D-Ala$^{10}$—LHRH.3TFA | | |
| 3546 | Ac-D-Nal$^1$, 4-Cl-D-Phe$^2$, D-Pal$^3$, Lys(TFAc)$^6$, Lys(iPr)$^8$, D-Ala$^{10}$—LHRH.2TFA | 6/8@1 μg | |
| 3570 | Ac-D-Nal$^1$, 4-Cl-D-Phe$^2$, D-Pal$^3$, Lys$^5$, D-Pal-(Bzl)$^6$, Lys(iPr)$^8$, D-Ala$^{10}$—LHRH.3TFA | | |
| 3571 | Ac-D-Nal$^1$, 4-Cl-D-Phe$^2$, D-Pal$^3$, Lys(iPr)$^5$, D-Lys-(Nic)$^6$, Lys(iPr)$^8$, D-Ala$^{10}$—LHRH.3TFA | | |
| 3572 | Ac-D-Nal$^1$, 4-Cl-D-Phe$^2$, D-Pal$^3$, Lys(iPr)$^5$, D-Lys-(Pic)$^6$, Lys(iPr)$^8$, D-Ala$^{10}$—LHRH.3TFA | | |
| | Ac-D-Nal$^1$, 4-Cl-D-Phe$^2$, D-Pal$^3$, Lys(TFAc)$^5$, D-Lys(TFAc)$^6$, Lys(iPr)$^8$, D-Ala$^{10}$—LHRH.2TFA | | |
| | Ac-D-Nal$^1$, 4-Cl-D-Phe$^2$, D-Pal$^3$, Lys(iPr)$^5$, 4-Cl-D-Phe$^6$, Lys(iPr)$^8$, D-Ala$^{10}$—LHRH.3TFA | | |
| | Ac-D-Nal$^1$, 4-Cl-D-Phe$^2$, D-Pal$^3$, Lys(iPr)$^5$, D-Nal$^6$, Lys(iPr)$^8$, D-Ala$^{10}$—LHRH.3TFA | | |

TABLE I-continued

LHRH Antagonists

| Compound | Sequence | AO activity (AOA) | Histamine release |
|---|---|---|---|
|  | Ac-D-Nal[1], 4-Cl-D-Phe[2], D-Pal[3], Lys(iPr)[5], D-Lys(pGlu)[6], Lys(iPr)[8], D-Ala[10]—LHRH.3TFA | | |
|  | Ac-D-Nal[1], 4-Cl-D-Phe[2], D-Pal[3], Lys(iPr)[5], D-Lys(OTac)[6], Lys(iPr)[8], D-Ala[10]—LHRH.3TFA | | |
|  | Ac-D-Nal[1], 4-Cl-D-Phe[2], D-Pal[3], Ile[5], D-Pal(Bzl)[6], Lys(iPr)[8], D-Ala[10]—LHRH.3TFA | | |
|  | Ac-D-Nal[1], 4-Cl-D-Phe[2], D-Pal[3], Lys(Pic)[5], D-Pal-(iPr)[6], Lys(iPr)[8], D-Ala[10]—LHRH.3TFA | | |
| 3721 | Ac-D-Nal[1], 4-Cl-D-Phe[2], D-Pal[3], D-Lys(3-Δ-Pro)[6], Lys(iPr)[8], D-Ala[10]—LHRH.TFA | 4/8@1.0 | |
| 3722 | Ac-D-Nal-4-Cl-D-Phe[2], D-Pal[3], D-Lys(Ac-D-Nal[1], 4-Cl-D-Phe[2], D-Pal[3], Ser)[6], Lys(iPr)[8], D-Ala[10]—LHRH.TFA | 8/8@5.0 | |
| 3723 | Ac-D-Qal[1], 4-Cl-D-Phe[2], D-Pal[3], D-Lys(pGlu)[6], Lys(iPr)[8], D-Ala[10]—LHRH.TFA | 7/8@1.0 | |
| 3740 | Ac-D-Qal[1], 4-Cl-D-Phe[2], D-Pal[3], D-Lys(Ac)[6], Lys(iPr)[8], D-Ala[10]—LHRH.TFA | 6/8@1.0 | |
| 3741 | Ac-D-Nal[1], 4-Cl-D-Phe[2], D-Pal[3], D-Lys(Imdac)[6], Lys(iPr)[8], D-Ala[10]—LHRH.TFA | 1/8@1.0<br>6/8@0.5 | |
| 3742 | Ac-D-Qal[1], 4-Cl-D-Phe[2], D-Pal[3], D-Lys(Dodac)[6], Lys(iPr)[8], D-Ala[10]—LHRH.TFA | 6/8@1.0 | |
| 3743 | Ac-D-Nal[1], 4-Cl-D-Phe[2], D-Pal[3], Ser[5], D-Pal(iPr)[6], Lys(iPr)[8], D-Ala[10]—LHRH.2TFA | 8/8@1.0 | |
| 3753 | Ac-D-Nal[1], 4-Cl-D-Phe[2], D-Pal[3], D-Lys(iPr)[5], D-Lys-(TFAc)[6], Lys(iPr)[8], D-Ala[10]—LHRH.2TFA | 7/8@1.0 | |
| 3754 | Ac-D-Nal[1], 4-Cl-D-Phe[2], D-Pal[3], His[5]D-Pal(iPr)[6], Lys(iPr)[8], D-Ala[10]—LHRH.2TFA | 5/8@1.0 | |
| 3744 | Ac-D-Nal[1], 4-Cl-D-Phe[2], D-Pal[3], Asn[5], D-Pal(iPr)[6], Lys(iPr)[8], D-Ala[10]—LHRH.2TFA | 7/8@1.0 | |
| 3745 | Ac-D-Nal[1], 4-Cl-D-Phe[2], D-Pal[3], Lys(iPr)[5], D-Lys-(4HBc)[6], Lys(iPr)[8], D-Ala[10]—LHRH.2TFA | 6/8@1.0 | |
| 3755 | Ac-D-Nal[1], 4-Cl-D-Phe[2], D-Pal[3], Met[5], D-Pal-(iPr)[6], Lys(iPr)[8], D-Ala[10]—LHRH.2TFA | 7/821.0 | |
| 3756 | Ac-D-Nal[1], 4-Cl-D-Phe[2], D-Phe[2], D-Pal[3], Ala[5], D-Pal(iPr)[6], Lys(iPr)[8], D-Ala[10]—LHRH.2TFA | 6/8@1.0 | |
| 3757 | Ac-D-Nal[1], 4-Cl-D-Phe[2], D-Pal[3], N—Me—Ala[5], D-Pal(iPr)[6], Lys(iPr)[8], D-Ala[10]—LHRH.2TFA | 7/8@1.0 | |
| 3758 | Ac-D-Nal[1], 4-Cl-D-Phe[2], D-Pal[3], D-Lys(Hippic)[6], Lys(iPr)[8], D-Ala[10]—LHRH.TFA | 5/8@1.0 | |
| 3759 | Ac-D-Nal[1], 4-Cl-D-Phe[2], D-Pal[3], D-Lys(AcGly)[6], Lys(iPr)[8], D-Ala[10]—LHRH.TFA | 5/8@1.0 | |
| 3760 | Ac-D-Nal[1], 4-Cl-D-Phe[2], D-Pal[3], D-Lys(Ppic)[6], Lys(iPr)[8], D-Ala[10]—LHRH.TFA | 1/8@1.0<br>7/8@0.5 | |
| 3761 | Ac-D-Nal[1], 4-Cl-D-Phe[2], D-Pal[3], D-Lys(Mts)[6], Lys-(iPr)[8], D-Ala[10]—LHRH.TFA | 7/8@1.0 | |
| 3762 | Ac-D-Nal[1], 4-Cl-D-Phe[2], D-Pal[3], D-Lys(Orotic)[6], Lys(iPr)[8], D-Ala[10]—LHRH.TFA | 6/8@1.0 | |
| 3763 | Ac—Sar[1], 4-Cl-D-Phe[2], D-Nal[3], D-Pal(Bzl)[6], Lys-(iPr)[8], D-Ala[10]—LHRH.2TFA | 4/8@1.0 | 102[1], 76[b] |
| 3769 | Ac—Sar[1], 4-Cl-D-Phe[2], 1-1-Nal[3], D-Pal(Bzl)[6], Lys-(iPr)[8], D-Ala[10]—LHRH.2TFA | 6/8@1.0 | |
| 3770 | Ac-D-Nal[1], 4-Cl-D-Phe[2], D-Pal[3], D-Pal(CH$_2$COOH)[6], Lys(iPr)[8], D-Ala[10]—LHRH.TFA | 6/8@1.0<br>0.1 DMSO | |
| 3771 | Ac-D-Nal[1], 4-Cl-D-Phe[2], D-Pal[3], D-Lys(Ala)[6], Lys-(iPr)[8], D-Ala[10]—LHRH.TFA | 7/8@1.0 | |
| 3772 | Ac—Sar[1], 4-Cl-D-Phe[2], D-1-Nal[3], D-Pal(iPr)[6], Lys-(iPr)[8], D-Ala[10]—LHRH.2TFA | 8/8@1.0 | |
| 3773 | Ac—Sar[1], 4-Cl-D-Phe[2], L-1-Nal[3], D-Pal(iPr)[6], Lys-(iPr)[8], D-Ala[10]—LHRH.2TFA | 7/8@1.0 | |
| 3785 | Ac-D-Qal[1], 4-Cl-D-Phe[2], D-Pal[3], D-Lys(Gulonyl)[6], Lys(iPr)[8], D-Ala[10]—LHRH.TFA | 7/8@1.0<br>0.1 DMSO | |
| 3786 | Ac-D-Nal[1], 4-Cl-D-Phe[2], D-Pal[3], D-Pal(N-O)[6], Lys-(iPr)[8], D-Ala[10]—LHRH.TFA | 4/8@1.0 | |
| 3787 | Ac-D-Qal[1], 4-Cl-D-Phe[2], D-Pal[3], D-Lys(Ppic)[6], Lys(iPr)[8], D-Ala[10]—LHRH.TFA | 7/8@1.0 | |
| 3800 | Ac-D-Qal[1], 4-Cl-D-Phe[2], D-Pal[3], D-Lys(Imdac)[6], Lys(iPr)[8], D-Ala[10]—LHRH.TFA | 7/8@1.0 | |
| 3801 | Ac-D-Qal[1], 4-Cl-D-Phe[2], D-Pal[3], D-Lys(Onic)[6], Lys(iPr)[8], D-Ala[10]—LHRH.TFA | 8/8@1.0 | |
| 3802 | Ac-D-Qal[1], 4-Cl-D-Phe[2], D-Pal[3], D-Lys(Otac)[6], Lys(iPr)[8], D-Ala[10]—LHRH.TFA | 5/8@1.0 | |
| 3803 | Ac-D-Nal[1], 4-Cl-D-Phe[2], D-Pal[3], D-Lys(Dodac)[6], Lys(iPr)[8], D-Ala[10]—LHRH.TFA | 2/8@1.0 | |
| 3804 | Ac-D-Pal[1], 4-Cl-D-Phe[2], D-Pal[3], D-Pal(iPr)[6], Lys- | 8/8@1.0 | |

TABLE I-continued

LHRH Antagonists

| Compound | Sequence | AO activity (AOA) | Histamine release |
|---|---|---|---|
| | (iPr)[8], D-Ala[10]—LHRH.2TFA | | |
| 3827 | Ac-D-Nal[1], 4-Cl-D-Phe[2], D-Pal[3], N—Me—Tyr[5], D-Asn[6], Lys(iPr)[8], D-Ala[10]—LHRH.TFA | 4/8@1.0 | |
| 3828 | Ac-D-Nal[1], 4-Cl-D-Phe[2], D-Pal[3], N—Me—Tyr[5], D-Lys(Onic)[8], Lys(iPr)[8], D-Ala[10]—LHRH.TFA | 4/8@1.0 | 42[a], 39[b] |
| 3829 | Ac-D-Nal[1], 4-Cl-D-Phe[2], D-Pal[3], N—Me—Tyr[5], D-Lys(Ac)[6], Lys(iPr)[8], D-Ala[10]—LHRH.TFA | 8/8@1.0 | |
| 3852 | Ac-D-Nal[1], 4-Cl-D-Phe[2], D-Pal[3], Lys(iPr)[5], D-His[6], Trp[7], Orn[8], D-Ala[10]—LHRH.TFA | 8/8@5.0 | |
| 3853 | Ac-D-Nal[1], 4-Cl-D-Phe[2], D-Pal[3], His[5], D-Arg[6], Trp[7], Orn[8], D-Ala[10]—LHRH.TFA | 0/8@5.0 | |
| 3854 | Ac-D-Nal[1], 4-Cl-D-Phe[2], D-Pal[3], Arg[5], D-His[6], Trp[7], Orn[8], D-Ala[10]—LHRH.TFA | 6/8@5.0 | |
| 3855 | Ac-D-Nal[1], 4-Cl-D-Phe[2], D-Pal[3], Lys(iPr)[5], D-Trp[6], Trp[7], Orn[8], D-Ala[10]—LHRH.TFA | 4/8@1.0 | |
| 3851 | Ac-D-Nal[1], 4-Cl-D-Phe[2], D-Pal[3], 4-Cl-Phe[5], D-Pal(iPr)[6], Lys(iPr)[8], D-Ala[10]—LHRH.2TFA | 0/8@1.0 6/8@0.5 | 4.1[a], 5.4[b] |
| 3882 | Ac-D-Nal[1], 4-Cl-D-Phe[2], D-Pal(N-O)[3], D-Pal(iPr)[6], Lys(iPr)[8], D-Ala[10]—LHRH.2TFA | 6/8@1.0 | |
| 3880 | Ac-D-Nal[1], 4-Cl-D-Phe[2], D-Trp[3], D-Arg[6], Met[8], D-Ala[10]—LHRH.TFA | 8/8@1.0 | |
| 3878 | Ac-D-Nal[1], 4-Cl-D-Phe[2], D-Trp[3], D-Arg[6], Met(S⁺Me)[8], D-Ala[10]—LHRH.2TFA | 2.8@1.0 7/8@0.5 | |
| 3881 | Ac-D-Nal[1], 4-Cl-D-Phe[2], D-Trp[3], D-Met[6], D-Ala[10]—LHRH.TFA | 7/8@1.0 | |
| 3879 | Ac-D-Nal[1], 4-Cl-D-Phe[2], D-Trp[3], D-Met(S⁺Me)[6], D-Ala[10]—LHRH.2TFA | 0/8@1.0 6/8@0.5 | |
| 3926 | Ac-D-Nal[1], 4-Cl-D-Phe[2], D-Trp[3], D-Arg[6], Lys(COCH₂Br)[8], D-Ala[10]—LHRH.TFA | 6/8@1.0 | |
| 3925 | Ac-D-Nal[1], 4-Cl-D-Phe[2], D-Trp[3], D-Met(S⁺Me)[6], Met(S⁺Me)[8], D-Ala[10]—LHRH.2TFA | 5/8@1.0 | 13[c], 5[d] |
| 3941 | Met(S⁺Me)[8]—LHRH.TFA | 8/8@50.0 | |
| 3942 | Lys(COCH₂Br)[8]—LHRH | 8/8@50.0 | |
| 3948 | Ac-D-Nal[1], 4-Cl-D-Phe[2], D-Trp[3], D-Lys(COCH₂Br)[6], D-Ala[10]—LHRH.TFA | low activity | |
| 3949* | Ac-D-Nal[1], 4-Cl-D-Phe[2], D-Pal[3], D-Lys(COCH₂CH₂N(Et)₂)[6], D-Ala[10]—LHRH.2TFA | low activity | |
| 3960 | Ac-D-Nal[1], 4-Cl-D-Phe[2], D-Pal[3], D-Lys(2-pyrimidyl-thio)acetic)[6], Lys(iPr)[8], D-Ala[10]—LHRH.TFA | 5/8@1.00 | |
| 3961 | Ac-D-Nal[1], 4-Cl-D-Phe[2], D-Trp[3], D-Met(S⁺CH₂C₆H₅)[6], D-Ala[10]—LHRH.2TFA | 4/8@2.00 3/8@1.00 | |
| 3967 | Ac-D-Nal[1], 4-Cl-D-Phe[2], D-Pal[3], D-Met(S⁺CH₃)[6], D-Ala[10]—LHRH.2TFA | 1/8@0.5 7/8@0.25 | 0.38[e], 0.15[f] |
| 3968* | Ac-D-Nal[1], 4-Cl-D-Phe[2], D-Pal[3], D-Met(S⁺CH₂COPh)[6], D-Ala[10]—LHRH.2TFA | 4/8@1.00 | |
| 3969 | Ac-D-Nal[1], 4-Cl-D-Phe[2], D-Pal[3], D-Dap(COCH₂S⁺Me₂)[6], D-Ala[10]—LHRH.2TFA | 3/8@1.00 | |
| 3982 | Ac-D-Nal[1], 4-Cl-D-Phe[2], D-Pal[3], His[5]D-Pal(iPr)[6], Lys(iPr)[8], D-Ala[10]—LHRH.2TFA | 8/8@1.00 | 53[c], 33[d] |
| 3983 | Ac-D-Nal[1], 4-Cl-D-Phe[2], D-Pal[3], D-Arg[6], Met(S⁺Me)[8], D-Ala[10]—LHRH.2TFA | 0/8@1.00 8/8@0.5 | 5.35[g], 1.32[h] |
| 3984 | Ac-D-Nal[1], 4-Cl-D-Phe[2], D-Trp[3], D-Met(S⁺CH₂—CH=CH₂)[6], D-Ala[10]—LHRH.2TFA | 3/8@1.00 | |
| 3985 | Ac-D-Nal[1], 4-Cl-D-Phe[2], D-Pal[3], D-Arg[6], Orn(COCH₂S⁺Me₂)[8], D-Ala[10], LHRH.2TFA | 0/8@1.00 8/8@0.5 | 4.4[a], 3.86[b] |
| 3994 | Ac-D-Nal[1], 4-Cl-D-Phe[2], D-Pal[3], D-Arg[6], Orn(COCH₂SMe)[8], D-Ala[10]—LHRH.2TFA | 6/8@1.00 | |
| 3995 | Ac-D-Nal[1], 4-Cl-D-Phe[2], D-Pal[3], D-Arg[6], Met[8], D-Ala[10]—LHRH.TFA | 5/8@1.00 | |
| 4014 | Ac-D-Nal[1], 4-Cl-D-Phe[2], D-Pal[3], D-Lys-(COCH₂S⁺Me₂)[6], D-Ala[10]—LHRH.2TFA | 0/8@1.00 | |
| 4015 | Ac-D-Nal[1], 4-Cl-D-Phe[2], D-Pal[3], D-Arg[6], Lys-(COCH₂S⁺Me₂)[8], D-Ala[10]—LHRH.2TFA | 1/8@1.00 | |
| 4016 | Ac-D-Nal[1], 4-Cl-D-Phe[2], D-Pal[3], D-Met(S⁺Me)[6], Met(S⁺Me)[8], D-Ala[10]—LHRH.2TFA | 6/8@1.00 | |
| 4013 | Ac-D-Nal[1], 4-Cl-D-Phe[2], D-Pal[3], D-Orn-(COCH₂S⁺Me₂)[6], D-Ala[10]—LHRH.2TFA | 0/8@1.00 | |
| 4023 | Ac-D-Nal[1], 4-Cl-D-Phe[2], D-Pal[3], D-Arg[6], Dap-(COCH₂S⁺Me₂)[8], D-Ala[10]—LHRH.2TFA | 0/8@1.00 | |

*= Mass spectral analysis did not confirm the structure,
Nal arg (reference) histamine release values: a = 0.11, b = 0.14, c = 0.28, d = 0.11, e = 0.1, f = 0.02, g = 0.1, h = 0.02

In a particularly preferred embodiment, the peptide comprises a structure: Ac-D-Nal-4-Cl-D-Phe-D-Pal-Ser-N-Me-Tyr-D-Asn-Leu-Lys(iPr)-Pro-D-Ala-NH$_2$; or a pharmaceutically acceptable salt thereof.

In another particularly preferred embodiment, the peptide comprises a structure: Ac-D-Nal-4-Cl-D-Phe-D-Pal-Ser-Tyr-D-Asn-Leu-Lys(iPr)-Pro-D-Ala-NH$_2$; or a pharmaceutically acceptable salt thereof.

Preferably, histamine-releasing activity is assayed by the method described in U.S. Pat. No. 4,851,385 to Roeske. The efficacy of candidate LHRH-R antagonists in inhibiting LH release can be assayed, for example, in an animal model such as that described in Corbin and Beattie, *Endocrine Res. Commun.* 2:1 (1975). In this assay, the LHRH-R antagonistic activity of a candidate compound is assayed by measuring the antiovulatory activity (AOA) of the compound in rats.

The term "LHRH-R agonist", as used herein, refers to a compound that stimulates the luteinizing hormone releasing hormone receptor such that luteinizing hormone is released (e.g., a compound that mimics the activity of LHRH). An LHRH-R agonist can have greater LH-releasing activity than natural LHRH (referred to as a "superagonist"). Many LHRH-R agonists and superagonists are known in the art. Commercially available LHRH agonists include leuprolide (trade name: Lupron®; Abbott/TAP), goserelin (trade name: Zoladex®; Zeneca), buserelin (Hoechst), decapeptyl (trade name: Debiopharm®3; Ipsen/Beaufour), nafarelin (Syntex), lutrelin (Wyeth), cystorelin (Hoechst), gonadorelin (Ayerst) and histrelin (Ortho). Preferred LHRH-R agonists are leuprolide, goserelin and decapeptyl.

For reviews of LHRH agonists and antagonists, see also B. H. Vickery et al., eds., (1984) "LHRH and Its Analogs: Contraceptive and Therapeutic Applications", MTP Press Limited, Lancaster, Pa.; and G. Schaison (1989) *J. Steroid Biochem.* 33(4B): 795. Exemplary LHRH agonist and antagonists useful in the methods of the present invention include nona- and decapeptides, as well as peptidomimetics, that mimic the structure of natural LHRH.

An "antiandrogen", as used herein, refers to a compound that antagonizes the release or action of androgens. Antiandrogens are known in the art (see, e.g., U.S. Pat. No. 4,386,080), and are commercially available (e.g., Androcur, a product of Schering A.G.). Candidate antiandrogens can be evaluated by methods known in the art (see, e.g., Goos et al., (1982) "An Improved Method of Evaluating Antiandrogens," *Arch. Dermatol. Res.*, 273:333–341). Antiandrogens can be steroidal or nonsteroidal. Preferred antiandrogens for use in the methods of the invention include nonsteroidal antiandrogens such as flutamide (4'-nitro-3'-trifluorormethyl isobutyranilide; available from Schering-Plough under the trade name Eulexin®), bicalutamide and nilutamide.

The term "inhibitor of sex steroid biosynthesis" is intended to include inhibitors of adrenal sex steroid biosynthesis (e.g., aminoglutethimide) and inhibitors of testicular sex steroid biosynthesis (e.g., ketoconazole), or combinations thereof. When an inhibitor of adrenal sex steroid biosynthesis is employed, it may be desirable to simultaneously administer hydrocortisone to the patient in an amount sufficient to maintain normal glucocorticoid levels.

Various aspects of the invention are described further in the following subsections.

I. Methods for Treating Prostate Cancer

The methods of the invention feature the administration of an LHRH-R antagonist in combination with a second therapy, such as performance of a procedure that removes or destroys tumor tissue or administration of an LHRH-R agonist.

One aspect of the invention pertains to a method for treating prostate cancer in a subject in need of such treatment, comprising administering to the subject an LHRH-R antagonist, and performing on the subject at least one procedure that removes or destroys prostatic tumor tissue, such as a radical prostatectomy, cryosurgery, external X-ray therapy or interstitial X-ray therapy (i.e., implantation of a radioactive seed). The type, dosage and duration of LHRH-R antagonist therapy are selected such that efficient blockade of androgen secretion is obtained without the occurrence of the flare reaction that accompanies the use of LHRH-R agonists in other treatment methods. Preferably, the LHRH-R antagonist is administered to the subject prior to performing the procedure that removes or destroys prostatic tumor tissue. For example, an LHRH-R antagonist can be used in neoadjuvant hormonal downstaging therapy prior to radical prostatectomy (or other procedure to remove or destroy tumor tissue). Administration of an LHRH-R antagonist is preferably for a period sufficient to cause the prostate or prostatic tumor tissue to shrink in size prior to performing the procedure that removes or destroys prostatic tumor tissue. A suitable period for preadministration of an LHRH-R antagonist typically is between about one month and about one year, more preferably between about three months and about six months.

Use of an LHRH-R antagonists in the combination treatment method is expected to sufficiently reduce androgen production such that additional use of an antiandrogen is not essential. However, in certain situations it may be desirable to use an antiandrogen and thus in another embodiment, this treatment method can further involve administering an antiandrogen to the subject in combination with the LHRH-R antagonist prior to performing the procedure that removes or destroys prostatic tumor tissue. Since use of LHRH-R antagonists avoid the flare reaction that occurs with LHRH-R agonists, it is expected that when an antiandrogen is used in combination with the LHRH-R antagonist, the dosage and duration of treatment with the antiandrogen would be reduced as compared to when an antiandrogen is used in combination with an LHRH-R agonist. In yet another embodiment, this treatment method can further involve administering one or more inhibitors of sex steroid biosynthesis to the subject in combination with the LHRH-R antagonist (optionally in further combination with an antiandrogen) prior to performing the procedure that removes or destroys prostatic tumor tissue.

Another aspect of the invention pertains to a method for treating prostate cancer in a subject in need of such treatment, comprising administering to the subject an LHRH-R antagonist; and simultaneously or subsequently administering to the subject an LHRH-R agonist. The type, dosage and duration of the combined LHRH-R antagonist and LHRH-R agonist therapy are selected such that the flare reaction is reduced or eliminated compared to when an LHRH-R agonist alone is used. Thus, the LHRH-R agonist should be administered simultaneously with, or subsequent to, initiation of LHRH-R antagonist administration, but not before. In a preferred embodiment, an LHRH-R antagonist is administered to a subject for at least one week before an LHRH-R agonist is administered to the subject. Once LHRH-R agonist therapy has been initiated, the LHRH-R antagonist therapy can be continued (i.e., the antagonist and the agonist can be coadministered) or the LHRH-R antagonist therapy can be discontinued (i.e., first the LHRH-R antagonist alone is administered to the subject and then the LHRH-R agonist alone is administered to the subject). In a preferred embodiment, an LHRH-R antagonist and an LHRH-R agonist are coadministered for a period of one month to one year, more preferably for about three to six months. In certain embodiments, a procedure that removes or destroys tumor tissue (e.g., a radical prostatectomy, cryosurgery or X-ray therapy) is performed after the administration of the LHRH-R antagonist and LHRH-R agonist.

As described above, while it may not be necessary to combine LHRH-R antagonist/LHRH-R agonist therapy with additional drugs, in certain situation it may be desirable to further combine the LHRH-R antagonist and LHRH-R agonist with other drugs, such as an antiandrogen and/or one or more inhibitors of sex steroid biosynthesis.

As is discussed in more detail below, a preferred route of administration for an LHRH-R antagonist (alone or in combination with an LHRH-R agonist) is by depot injection or other slow-release or sustained delivery method. A preferred route of antiandrogen administration is oral administration. Radical prostatectomy, cryosurgery and/or X-ray therapy (external or interstitial) can be performed using standard methodologies.

The methods of the present invention can be applied to the treatment of prostate cancer in male subjects at any stage of the cancer, although certain treatment methods are more preferred for particular cancer stages. For reviews on screening and diagnostic methods for prostate cancer, see e.g., Garnick, M. (1993) *Annals of Internal Medicine* 118:803–818; and Garnick, M. (1994) *Scientific American* 270:72–81. Prostate cancer is commonly evaluated according to a scale divided into four lettered stages: A, B, C and D. Tumors in stage A are microscopic; stage $A_1$ designates tumors confined to a relatively small area and composed of well-differentiated tissue, while stage $A_2$ tumors are more diffuse and less well differentiated. Stage B tumors are large enough to be felt during a rectal examination, while stage C prostate cancers have spread throughout the gland and typically have pushed past the borders of the prostate into surrounding structures. Stage D tumors have metastasized, e.g. to lymph nodes, bone, or other organs. Alternatively, tumors can be staged by the TNM staging system, in which tumors are ranked on a scale of progressively worsening disease from T1a to T4b (e.g., T1c tumors are non-palpable and non-visible that were detected by elevated blood levels of prostate specific antigen). The methods of the invention are useful in the treatment of any stage of prostate cancer. However, it will be appreciated by the skilled artisan that methods involving procedures for removal or destruction of prostatic tumor tissue preferably are employed with non-metastasized cancers. For example, radical prostatectomy preferably is used with stage A, B and some stage C tumors (i.e., where the tumor growth has not extended considerably beyond the borders of the prostate gland) as well as stage T1c tumors. X-ray therapy (e.g., external or interstitial) preferably is used with stage A, B or C tumors as well as T1c tumors.

To assess the efficacy of a treatment method of the invention, the size of the prostate can be determined by methods known in the art, for example, rectal examination, transrectal ultrasonography or magnetic resonance imaging (MRI). Moreover, the size or extent of the prostate tumor (and metastatic tumors, if any) can be assessed by known methods including a prostate-specific antigen blood test (described further below), bone scanning, X-rays, skeletal survey, intravenous pyelography, CAT-scan, MRI, physical examination, biopsy, and the like. For treatment methods that involve surgery (e.g., in neoadjuvant therapy wherein an LHRH-R antagonist is administered prior to a radical prostatectomy), the tumor can also be staged during surgery (e.g., the prostate gland can be examined during surgery and/or a biopsy can be taken and examined). Thus, clinical staging and/or surgical staging may be used to evaluate the extent of disease. Use of an LHRH-R antagonist in accordance with the methods of the invention is expected to result in a tumor stage, assessed at the time of radical prostatectomy, that is improved compared to methodologies utilizing an LHRH-R agonist.

A preferred method of evaluating the extent of prostate cancer is to assay the level of prostate-specific antigen (PSA) in a subject's blood. The PSA blood test is a reasonably specific, sensitive, rapid, and inexpensive tool for screening for prostate cancer. In general, a blood PSA level above 4 ng/ml is considered to be suggestive of the presence of prostate cancer, with levels above 10 ng/ml being particularly indicative of cancer. For a subject undergoing treatment with an LHRH-R antagonist according to the methods of the invention, a pretreatment level of PSA can be established and the efficacy of the treatment assessed by monitoring periodically the PSA level in the subject's blood, wherein decreased PSA levels are used as an indicator of the efficacy of the treatment. The PSA nadir (i.e., the point at which PSA levels do not decrease farther even upon further treatment with an LHRH-R antagonist) can be used as the indicator point for initiation of a second therapy, for example for performance of a procedure that removes or destroys prostatic tumor tissue (such as radical prostatectomy, cryosurgery and/or external or interstitial X-ray therapy). It is expected that the PSA nadir will be reached sooner using an LHRH-R antagonist, as compared to an LHRH-R agonist, since the flare reaction is avoided using an LHRH-R antagonist.

Additionally or alternatively, plasma concentrations of sex hormones can be monitored to assess the efficacy of the drug therapy. Concentrations of hormones such as testosterone, dihydrotestosterone, dehydroepiandrosterone (DHEA), DHEA-sulfate, androst-5-ene-3β, 17β-diol, and the estrogen 17β-estradiol can all be measured by methods known the skilled artisan (see, e.g., F. Labrie et al., (1983) *The Prostate* 4:579). Preferably, decreased levels of testosterone and dihydrotestosterone are used as indicators of treatment efficacy.

The response criteria for prostate developed by the National Prostate Cancer Project (see e.g., *The Prostate*, 1:375–382) can also be used to assess the efficacy of treatment. For treatment methods involving a procedure that removes or destroys tumor tissue (such as radical prostatectomy, cryosurgery or external or interstitial X-ray therapy), it is preferable to administer an LHRH-R antagonist until the size of the prostate or a prostate tumor has decreased and/or blood PSA levels have decreased before performing the procedure.

Although the methods of the invention are described in particular with application to the treatment of prostate cancer, it will be appreciated by the skilled artisan that these methods also can be applied to the treatment of other sex hormone-dependent cancers, such as ovarian cancer or breast cancer, in humans or animals of either sex. In such cases, methods involving a step comprising surgical removal of tumor tissue are designed for the removal of the tumor tissue of the particular cancer to be treated.

II. Pharmaceutical Compositions

LHRH-R antagonists suitable for use in the methods of the invention can be incorporated into pharmaceutical compositions suitable for administration to a subject. Preferably, an LHRH-R antagonist alone is formulated into the pharmaceutical composition, although in certain embodiments the LHRH-R antagonist may be combined with one or more other drugs such as an LHRH-R agonist, antiandrogen and/or inhibitor of sex steroid biosynthesis (collectively referred to as "combination drug(s)"). In a preferred embodiment, the pharmaceutical composition comprises an LHRH antagonist and a pharmaceutically acceptable carrier.

A "therapeutically effective amount" refers to an amount effective, at dosages and for periods of time necessary, to achieve the desired result. A therapeutically effective amount of an LHRH-R antagonist may vary according to factors such as the disease state, age, and weight of the individual, and the ability of the LHRH-R antagonist (alone or in combination with one or more combination drugs) to elicit a desired response in the individual. Dosage regimens may be adjusted to provide the optimum therapeutic response. A therapeutically effective amount is also one in which any toxic or detrimental effects of the antagonist are outweighed by the therapeutically beneficial effects. A nonlimiting range for a therapeutically effective amount of an LHRH-R antagonist is 0.01 µg/kg–10 mg/kg, preferably between about 0.01 and 5 mg/kg. It is to be noted that dosage values may vary with the severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous or parenteral administration (e.g., by injection). Depending on the route of administration, the active compound may be coated in a material to protect the compound from the action of acids and other natural conditions which may inactivate the compound.

An LHRH-R antagonist can be administered by a variety of methods known in the art. In a preferred embodiment, the LHRH-R antagonist is administered in a time release formulation, for example in a composition which includes a slow release polymer, or by depot injection. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978. Particularly preferred formulations include controlled-release compositions such as are known in the art for the administration of leuprolide (trade name: Lupron®), e.g., microcapsules (U.S. Pat. Nos. 4,652,441 and 4,917,893), injectable formulations (U.S. Pat. No. 4,849,228), lactic acid-glycolic acid copolymers useful in making microcapsules or injectable formulations (U.S. Pat. Nos. 4,677,191 and 4,728,721), and sustained-release compositions for water-soluble polypeptides (U.S. Pat. No. 4,675,189).

When appropriately formulated, an LHRH-R antagonist may be orally administered, for example, with an inert diluent or an assimilable edible carrier. The LHRH-R antagonist and other ingredients may also be enclosed in a hard or soft shell gelatin capsule, compressed into tablets, or incorporated directly into the subject's diet. For oral therapeutic administration, the LHRH-R antagonist may be incorporated with excipients and used in the form of ingestible tablets, buccal tablets, troches, capsules, elixirs, suspensions, syrups, wafers, and the like. The percentage of the LHRH-R antagonist in the compositions and preparations may, of course, be varied. The amount of the LHRH-R antagonist in such therapeutically useful compositions is such that a suitable dosage will be obtained.

To administer an LHRH-R antagonist (alone or with one or more combination drugs) by other than parenteral administration, it may be necessary to coat the compound with, or co-administer the compound with, a material to prevent its inactivation. For example, the LHRH-R antagonist may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., (1984) *J Neuroimmunol.* 7:27). Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin.

Sterile injectable solutions can be prepared by incorporating the active compound (e.g., LHRH-R antagonist) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

This invention is further illustrated by the following examples which should not be construed as limiting. The contents of all references, patents and published patent applications cited throughout this application are hereby incorporated by reference.

EXAMPLE 1

A human subject with a localized prostate tumor (e.g., Stage B) is treated according to a method of the invention as follows:

An LHRH-R antagonist having low histamine-releasing activity is administered in a depot formulation by intramuscular injection of 10 mg of the LHRH-R antagonist in lactic acid/glycolic acid copolymer microcapsules (microcapsules are prepared as described in U.S. Pat. No. 4,849,228) or, alternatively, using a suitable pump for continuous drug delivery. Additional depot injections are administered each month, typically for a total treatment period of three to six months (although longer treatment periods can be used according to the individual need and the professional judgment of the person supervising the therapy). The size and progression of the prostate tumor is monitored by transrectal ultrasonography, rectal examination, and assay for prostate-specific antigen. A radical prostatectomy, cryosurgery, or X-ray therapy (external or interstitial) is performed by standard techniques when the prostate tumor has decreased in size or extent and/or the PSA nadir has been reached. LHRH-R antagonist administration can be continued following radical prostatectomy, cryosurgery or X-ray therapy according to the individual need and the professional judgment of the person supervising the therapy.

EXAMPLE 2

A human subject with a localized (e.g., Stage B) prostate cancer is treated with an LHRH-R antagonist as described in Example 1. After one month of treatment with the LHRH-R antagonist, an LHRH-R agonist (e.g., leuprolide, goserelin or decapeptyl) is administered. For example, leuprolide is administered in a depot formulation by intramuscular injection of 7.5 mg of leuprolide in lactic acid/glycolic acid copolymer microcapsules (microcapsules are prepared as described in U.S. Pat. No. 4,849,228). Oral flutamide (250 mg every 8 hours) is also begun. Treatment with the LHRH-R antagonist is continued such that the subject is treated with the LHRH-R antagonist, leuprolide and flutamide in combination. The progression of the prostate tumor is monitored as described in Example 1. If necessary, after a period of treatment sufficient to reduce the size and progression of the prostate tumor or reach the PSA nadir (e.g., three to six months), a radical prostatectomy, cryosurgery or X-ray therapy (external or interstitial) is performed by standard techniques.

EXAMPLE 3

A human subject with metastasized (e.g., Stage D) prostate cancer is treated with an LHRH-R antagonist as described in Example 2 for one month after which time LHRH-R antagonist therapy is discontinued and the subject is further treated with a combination of an LHRH-R agonist (e.g., leuprolide, goserelin or decapeptyl) and an antiandrogen (e.g., flutamide), also as described in Example 2, thus ameliorating the flare reaction expected to be produced by use of an LHRH-R agonist.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method for treating prostate cancer in a subject in need of such treatment, comprising:

administering to the subject an LHRH-R antagonist; and performing a procedure on the subject that removes or destroys prostatic tumor tissue.

2. The method of claim 1, wherein the LHRH-R antagonist is administered to the subject prior to performing the procedure that removes or destroys prostatic tumor tissue.

3. The method of claim 2, wherein the LHRH-R antagonist is administered for about 3 to 6 months prior to performing procedure that removes or destroys prostatic tumor tissue.

4. The method of claim 2, wherein the LHRH-R antagonist is administered for about 6 to 12 months prior to performing procedure that removes or destroys prostatic tumor tissue.

5. The method of claim 2, wherein administration of the LHRH-R antagonist to the subject is continued after performing the procedure that removes or destroys prostatic tumor tissue.

6. The method of claim 1, wherein the procedure that removes or destroys prostatic tumor tissue is a radical prostatectomy.

7. The method of claim 1, wherein the procedure that removes or destroys prostatic tumor tissue is cryosurgery.

8. The method of claim 1, wherein the procedure that removes or destroys prostatic tumor tissue is external X-ray therapy.

9. The method of claim 1, wherein the procedure that removes or destroys prostatic tumor tissue is interstitial X-ray therapy.

10. The method of claim 1, wherein the LHRH-R antagonist has an $ED_{50}$ for histamine release in a standard in vitro histamine release assay of at least 3 µg/ml.

11. The method of claim 1, wherein the LHRH-R antagonist has an $ED_{50}$ for histamine release in a standard in vitro histamine release assay of at least 5 µg/ml.

12. The method of claim 1, wherein the LH4RH-R antagonist has an $ED_{50}$ for histamine release in a standard in vitro histamine release assay of at least 10 µg/ml.

13. The method of claim 2, further comprising administering to the subject an antiandrogen in combination with the LHRH-R antagonist prior to performing the procedure that removes or destroys prostatic tumor tissue.

14. The method of claim 13, wherein the antiandrogen is a steroidal antiandrogen.

15. The method of claim 13, wherein the antiandrogen is a nonsteroidal antiandrogen.

16. The method of claim 15, wherein the antiandrogen is flutamide.

17. The method of claim 15, wherein the antiandrogen is bicalutamide.

18. The method of claim 15, wherein the antiandrogen is nilutamide.

19. The method of claim 2, farther comprising administering to the subject at least one inhibitor of sex steroid biosynthesis in combination with the LHRH-R antagonist prior to performing the procedure that removes or destroys prostatic tumor tissue.

20. The method of claim 1, wherein said LHRH-R antagonist has the following structure: Ac-D-Nal-4-Cl-D-Phe-D-Pal-Ser-N-Me-Tyr-D-Asn-Leu-Lys(iPr)-Pro-D-Ala-$NH_2$.

21. A method for destroying all or part of an LHRH responsive tissue in a subject, comprising:

administering to the subject an LHRH-R antagonist, at a dose and for a duration of time sufficient to reduce the size of the LHRH responsive tissue; and performing interstitial X-ray therapy to said tissue, thereby destroying all or part of said LHRH responsive tissue in the subject.

22. The method of claim 21, wherein said LHRH-R antagonist has the following structure: Ac-D-Nal-4-Cl-D-Phe-D-Pal-Ser-N-Me-Tyr-D-Asn-Leu-Lys(iPr)-Pro-D-Ala-$NH_2$.

* * * * *